United States Patent
Kozlow et al.

(10) Patent No.: US 10,520,481 B2
(45) Date of Patent: Dec. 31, 2019

(54) HYDROGEN SULFIDE GAS DETECTOR WITH HUMIDITY AND TEMPERATURE COMPENSATION

(71) Applicant: Rosemount Inc., Shakopee, MN (US)

(72) Inventors: Henryk Kozlow, Calgary (CA); Alastair Kerr Muir, Calgary (CA); Todd Christopher Phelps, Calgary (CA); Lucjan Antoni Oleszczuk, Calgary (CA)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 14/288,636

(22) Filed: May 28, 2014

(65) Prior Publication Data
US 2014/0356971 A1    Dec. 4, 2014

Related U.S. Application Data (60) Provisional application No. 61/828,263, filed on May 29, 2013.

(51) Int. Cl.
*G01N 33/00* (2006.01)
*G01N 27/414* (2006.01)
*G01N 27/12* (2006.01)

(52) U.S. Cl.
CPC ..... *G01N 33/0044* (2013.01); *G01N 27/4141* (2013.01); *G01N 27/12* (2013.01); *Y10T 436/184* (2015.01)

(58) Field of Classification Search
CPC ............... G01N 27/12; G01N 33/0044; G01N 27/4141; G01N 2033/0095
See application file for complete search history.

(56) References Cited

U.S. PATENT DOCUMENTS

| 4,157,283 | A | * | 6/1979 | Zetter | ................... E21B 49/005 204/412 |
| 4,542,640 | A | * | 9/1985 | Clifford | ............... G01N 27/122 422/98 |
| 4,730,479 | A |   | 3/1988 | Pyke et al. | |
| 5,171,372 | A |   | 12/1992 | Recine, Sr. | |

(Continued)

FOREIGN PATENT DOCUMENTS

EP    2085773 A1    8/2009
JP    56011349    2/1981

(Continued)

OTHER PUBLICATIONS

Search Report and Written Opinion from International Application No. PCT/US2014/039761, date of filing: May 28, 2014, dated Oct. 29, 2014. 15 pages.

(Continued)

*Primary Examiner* — Lyle Alexander
*Assistant Examiner* — Dwan A Gerido
(74) *Attorney, Agent, or Firm* — Christopher R. Christenson; Kelly, Holt & Christenson PLLC (57) ABSTRACT

A hydrogen sulfide gas detector is provided. The detector includes a metal oxide semiconductor-based hydrogen sulfide gas sensor having an electrical characteristic that varies with hydrogen sulfide gas concentration. Measurement circuitry is coupled to the metal oxide semiconductor-based hydrogen sulfide gas detector to measure the electrical characteristic. A controller is coupled to the measurement circuitry and is configured to receive an indication of the electrical characteristic of the hydrogen sulfide gas sensor as well as an indication of ambient humidity. The controller is configured to provide a compensated hydrogen sulfide gas concentration output based on the indication of the electrical characteristic of the hydrogen sulfide gas sensor, an indication of ambient temperature, and the indication of ambient humidity.

7 Claims, 5 Drawing Sheets

(56) References Cited

U.S. PATENT DOCUMENTS

| | | | | |
|---|---|---|---|---|
| 5,553,006 | A | * | 9/1996 | Benda .................. G08B 21/14 340/3.31 |
| 5,789,659 | A | * | 8/1998 | Williams .............. G01N 27/12 204/411 |
| 5,841,021 | A | * | 11/1998 | De Castro .......... G01N 27/4162 204/424 |
| 7,992,426 | B2 | | 8/2011 | Fleischer et al. |
| 8,578,758 | B2 | | 11/2013 | Ito |
| 2003/0019275 | A1 | | 1/2003 | Lloyd et al. |
| 2003/0042151 | A1 | | 3/2003 | Ando et al. |
| 2005/0072212 | A1 | | 4/2005 | Oishi et al. |
| 2009/0141767 | A1 | | 6/2009 | Cummins |
| 2009/0255350 | A1 | | 10/2009 | Decker |
| 2010/0303605 | A1 | | 12/2010 | Odle et al. |
| 2011/0303953 | A1 | | 12/2011 | Kamata |
| 2014/0182358 | A1 | | 7/2014 | Feng et al. |

FOREIGN PATENT DOCUMENTS

| | | |
|---|---|---|
| JP | 07082003 | 9/1995 |
| JP | 2004354225 | 12/2004 |
| JP | 2010054355 | 3/2010 |
| WO | WO03016877 A1 | 2/2003 |

OTHER PUBLICATIONS

International Search Report and Written Opinion from International Application No. PCT/US2013/077931, dated Apr. 21, 2014, date of filing: Dec. 27, 2013. 10 pages.

V. E. Bochenkov, G. B. Sergeev., Chapter 2 of Metal Oxide Nanostructure and Their Applications, "Sensitivity, Slecetivity, and Stability of Gas Sensitive Metal-Oxide Nanostructures", vol. 3, pp. 31-52.

Brochure "Complete Analytical & Monitoring Solutions", 24 pages. Available at: http://www2.emersonprocess.com.

"Detecting Hydrogen Sulfide Gas and Understanding its Danger in the Field" Published: Apr. 2013, 5 pages.

"Eco-Sense Electrochemical H2S, 2-wire, Loop-powered Gas Detector" Product Data Sheet. Published: Jul. 2012, 2 pages.

First Office Action for Chinese Patent Application 201480006372.3 dated Aug. 1, 2016, 11 pages.

Extended European Search Report for European Patent Application No. 14803768.2 dated Dec. 14, 2016, 9 pages.

Second Office Action for Chinese Patent Application No. 201480006372.3, dated Mar. 23, 2017, 20 pages with English Translation.

Third Office Action for Japanese Patent Application No. 201480006372.3, dated Sep. 20, 2017, 11 pages including English translation.

Fourth Office Action dated Feb. 11, 2018, for Chinese Patent Application No. 201480006372.3, 7 pages including English translation.

EPO Communication pursuant to Article 94(3) EPC, dated Jun. 7, 2018, for European Patent Application No. 14803768.2, 4 pages.

European Communication pursuant to Article 94(3) EPC dated Oct. 11, 2019, for European Patent Application No. 14803768.2, 5 pages.

* cited by examiner

HYDROGEN SULFIDE GAS DETECTOR WITH HUMIDITY AND TEMPERATURE COMPENSATION

CROSS-REFERENCE TO RELATED APPLICATION

The present application is based on and claims the benefit of U.S. Provisional Patent Application Ser. No. 61/828,263, filed May 29, 2013, the content of which is hereby incorporated in its entirety.

BACKGROUND

Hydrogen sulfide gas is deadly even at low concentrations. Generally, when one is exposed to hydrogen sulfide gas, it is imperative to seek medical attention relatively quickly. Accordingly, in many industrial situations, it is very important to be able to detect the gas in very low concentrations as soon as possible when a leak occurs, even in the most challenging and remote conditions.

Health and safety standards in many countries have been slowly decreasing the acceptable exposure levels as sensor response times and overall stability of sensing elements has improved. For example, in the United States, the Occupational Safety and Health Administration (OSHA) provides an acceptable concentration limit for exposure to hydrogen sulfide at 20 parts per million (ppm) for an 8-hour period, with the maximum peak exposure at 50 ppm for 10 minutes. The UK Health and Safety Executive specifies the maximum acceptable concentration for an 8 hour period at 5 ppm, with the maximum peak exposure for an 8 hour period at 10 ppm. A short-term exposure to even 500-1000 ppm can be life threatening and can cause serious harm. Higher concentrations can cause instant death. There is also evidence that repeated exposure to hydrogen sulfide gas in low concentrations can cause a variety of undesirable medical conditions including photophobia, conjunctivitis, corneal bullae, extreme pain and temporary loss of vision.

An important goal of any fixed-location hydrogen sulfide detector is to safeguard workers and the public by warning of the presence of hazardous levels of hydrogen sulfide in the proximity. Electrochemical and metal oxide semiconductor (MOS) cells have, for many years, been field-proven toxic sensing technologies. Metal oxide semiconductors have a long life compared to electrochemical sensors and continue to operate in wide ranging temperatures, particularly high temperatures, as well as in extremely dry conditions.

In some implementations, a hydrogen sulfide sensor is constructed as a sandwich of a platinum heater element, an insulation medium and the gas sensitive resistive film. In other implementations, a hydrogen sulfide sensor is constructed as a bead having a heater disposed therein and a leadwire running through the bead. The bead is formed of a gas-sensitive semiconductor. This gas sensitive material will employ traditional metal oxide semiconductor materials or metal oxide semiconductor materials that are enhanced at the nano-level to dramatically improve performance. During operation, when hydrogen sulfide gas comes into contact with the gas sensitive material, there is a measurable change in the electrical conductivity. These changes are typically amplified using electronics in a detector device.

The recent advances in nano-enhanced material construction have been able to effectively deal with some of the challenges that limited traditional metal oxide semiconductors. While the appearance and operating principle of a nano-enhanced metal oxide semi-conductor (NE-MOS) is identical to that of a traditional MOS sensor, NE-MOS benefits from a mechanically conformed array of sensing components known as "nanotubes" being applied to the resistive film in a manner in which they are perfectly aligned, symmetric, and extremely concentrated during the manufacturing process. Traditional MOS materials are produced using a process that leaves gaps and creates irregularities, resulting in performance challenges. Nano-enhanced materials provide increased overall sensing capability, faster response, and much higher stability.

As the technology of hydrogen sulfide gas sensors improves and sensing becomes more precise, changes in response of the sensor to hydrogen sulfide caused by changes in environmental conditions become dominant in determining the precision of the sensor. Providing a hydrogen sulfide gas detector that is better able to operate in a wide variety of environments represents an important advance in sensing hydrogen sulfide gas.

SUMMARY

A hydrogen sulfide gas detector is provided. The detector includes a metal oxide semiconductor-based hydrogen sulfide gas sensor having an electrical characteristic that varies with hydrogen sulfide gas concentration. Measurement circuitry is coupled to the metal oxide semiconductor-based hydrogen sulfide gas detector to measure the electrical characteristic. A controller is coupled to the measurement circuitry and is configured to receive an indication of the electrical characteristic of the hydrogen sulfide gas sensor as well as an indication of ambient humidity. The controller is configured to provide a compensated hydrogen sulfide gas concentration output based on the indication of the electrical characteristic of the hydrogen sulfide gas sensor, an indication of ambient temperature, and the indication of ambient humidity.

DETAILED DESCRIPTION OF ILLUSTRATIVE EMBODIMENTS

Both of the metal oxide semiconductor-type hydrogen sulfide gas detectors described above are susceptible to errors caused by changes in environmental humidity and temperature. Metal oxide semiconductor-type hydrogen sulfide gas sensors generally exhibit a cross-sensitivity to moisture, which affects the accuracy of the measurement. In using a metal oxide semiconductor-type gas sensor for hydrogen sulfide detection for gas concentrations at the ppm level, the effects of normal changes in levels of environmental humidity and temperature become quite significant. Embodiments of the present invention generally provide for, or employ an absolute humidity measurement system and temperature measurement system that are able to obtain an indication of environmental conditions and compensate the hydrogen sulfide sensor signal for such humidity and temperature in order to provide an improved accuracy hydrogen sulfide gas measurement.

In accordance with embodiments of the present invention, humidity and temperature measurement systems, in one example, a relative humidity and temperature measurement system, is added or otherwise employed with a hydrogen sulfide gas detector. The detector employs a metal oxide semiconductor to sense hydrogen sulfide gas. Once the humidity and temperature measurement system provides an indication of the environmental conditions, the hydrogen sulfide gas sensor output is compensated for the measured humidity and temperature. In one embodiment, the hydrogen sulfide gas sensor output is treated with an equation for the calculation of hydrogen sulfide concentration as follows:

$$\log(ppm)=\beta_1+\beta_2(\log(\text{Resistance}))+\beta_3(\text{temperature})+\beta_4(\text{waterContent})+\beta_5(\text{temperature})^2+\beta_6(\text{waterContent})^2+\beta_7(\log(\text{Resistance})^2)+\beta_8(\text{temperature}\cdot\log(\text{Resistance}))+\beta_9(\text{temperature}\cdot\text{waterContent})+\beta_{10}(\text{waterContent}\cdot\log(\text{Resistance}))+\beta_{11}(\text{waterContent}\cdot\log(\text{temperature})\cdot(\log(\text{Resistance})))$$

Where:
Resistance—is the solid state sensor resistance;
$\beta_1$-$\beta_{11}$—are coefficients;
ppm—is the target gas concentration, in parts per million;
temperature—is the system measured temperature;
waterContent—is the current water vapor content in the atmosphere, expressed as a ratio of water weight to the total water weight of air in a volume unit using indications for ambient relative humidity and temperature.

Figure 1:
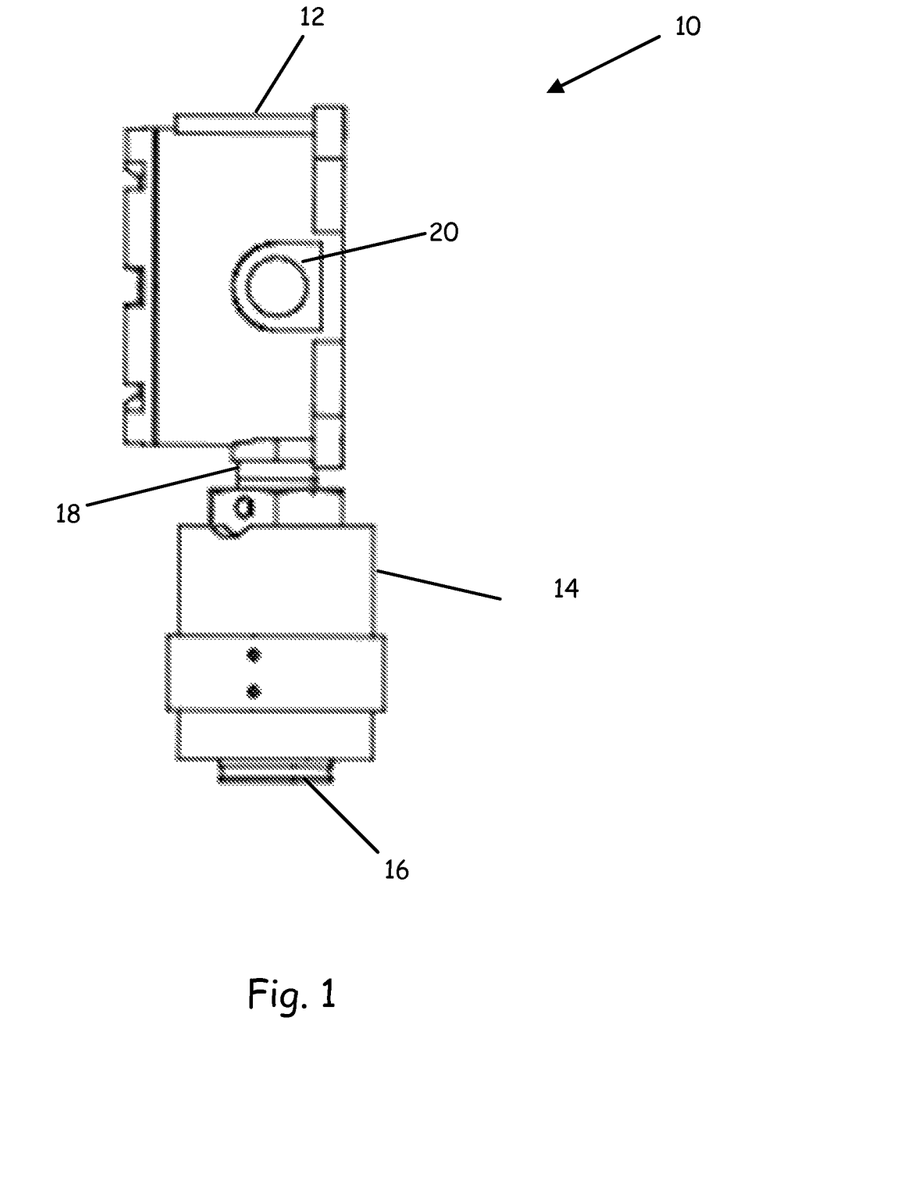
FIG. 1 is a diagrammatic view of a hydrogen sulfide gas detector with which embodiments of the present invention are particularly useful.

FIG. 1 is a diagrammatic view of a hydrogen sulfide gas detector with which embodiments of the present invention are particularly useful. Detector 10 includes electronics enclosure 12 coupled to sensor body 14. Sensor body 14 includes a metal oxide semiconductor-based hydrogen sulfide gas sensor (shown in FIG. 2) which may be a "traditional" metal oxide semiconductor sensor or an NE-MOS based semiconductor gas sensor. Lower portion 16 of sensor body 14 is configured to expose the hydrogen sulfide gas sensor to ambient air in order to determine a concentration of hydrogen sulfide gas in the ambient air. The sensor within sensor body 14 is coupled to suitable electronics (shown in FIG. 2) within enclosure 12 via conduit 18. Electronics within enclosure 12 can amplify, linearize, and otherwise characterize the sensor response in order to provide an indication of hydrogen sulfide gas concentration. This indication can be provided over a process communication loop or segment, via process wiring through conduit 20, as well as provided locally. A local indication of hydrogen sulfide gas detection can include a local operator interface indicating a display of hydrogen sulfide gas concentration, an audible or visual alarm, or any combination thereof.

Figure 2:
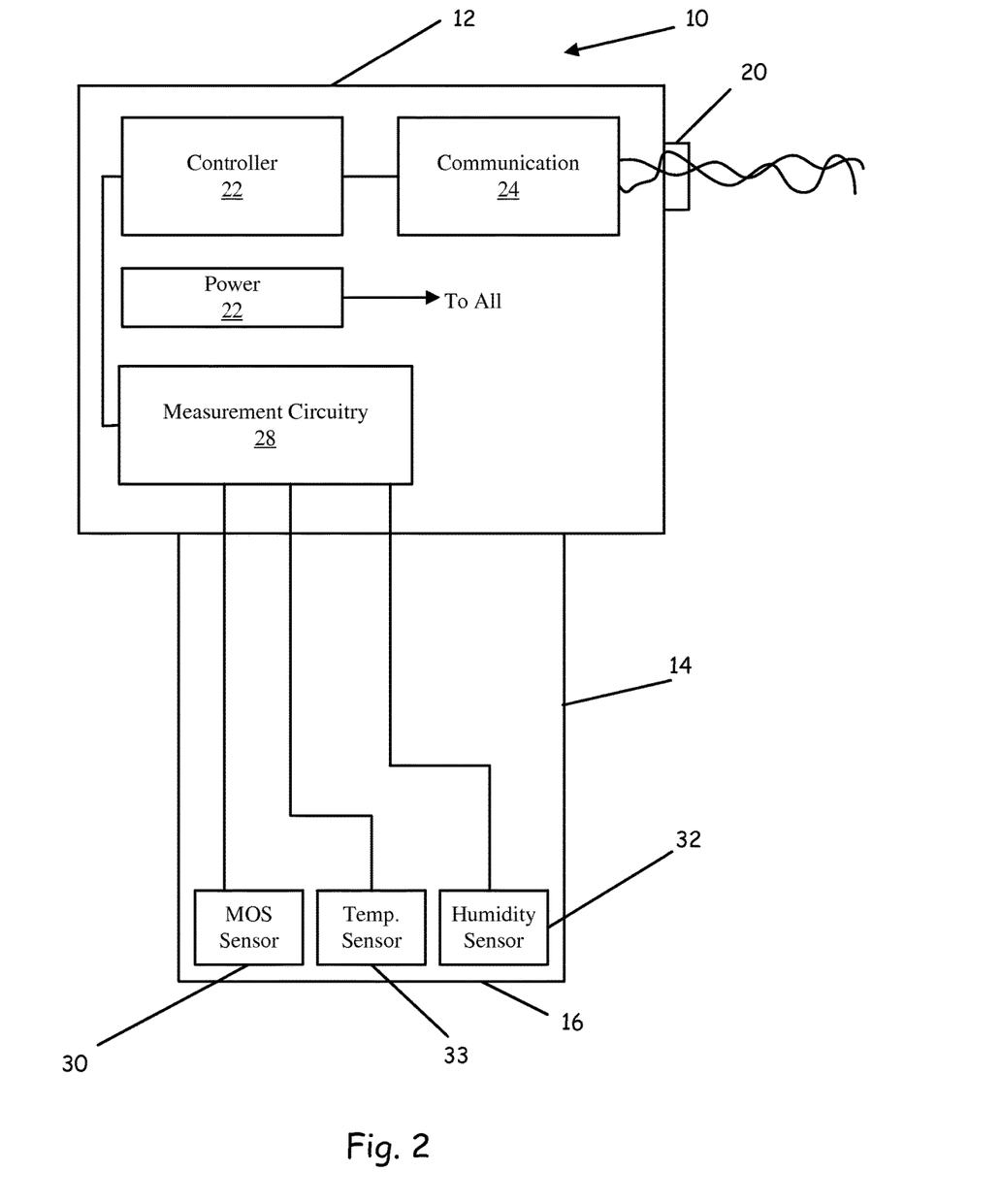
FIG. 2 is a block diagram of a hydrogen sulfide gas detector in accordance with an embodiment of the present invention.

FIG. 2 is a block diagram of a hydrogen sulfide gas detector in accordance with an embodiment of the present invention. Detector 10 includes electronics enclosure 12 coupled to sensor body 14. Disposed within electronics enclosure 12 are controller 22, communication module 24, power module 26, and measurement circuitry 28. Metal oxide semiconductor-based hydrogen sulfide gas sensor 30 is disposed within sensor body 14 and is coupled to measurement circuitry 28. Additionally, in accordance with an embodiment of the present invention, humidity sensor 32 and temperature sensor 33 are also disposed within sensor body 14 and are operably coupled to measurement circuitry 28.

Controller 22 may be any suitable processing circuitry that is able to apply the humidity and temperature compensation in accordance with embodiments of the present invention. In one embodiment, controller 22 is a microprocessor. Controller 22 is coupled to communication circuitry 24 to allow controller 22 to communicate with other devices in the process control and monitoring system. Communication circuitry 24 can include circuitry that allows controller 22 to communicate in accordance with process industry standard communication protocols, such as the Highway Addressable Remote Transducer (HART®) protocol, the FOUNDATION™ Fieldbus protocol, and others. Additionally, in some embodiments, device 10 may communicate wirelessly in addition to or instead of using wired process communication. For example, in one embodiment, communication circuitry 24 may allow communication in accordance with IEC62591. Finally, communication circuitry 24 may provide communication of local outputs, such as a local display, or alarm.

Power module 26 is coupled to all components within enclosure 12, as indicated by the arrow labeled "To All." Power module 26 is configured to receive power from a suitable source and provide voltage adjustment or other suitable power conditioning to the circuitry within enclosure 12. In some embodiments, power module 26 may be coupled to a wired process communication loop such that device 10 can receive all of its operating energy from the wired process communication loop. In other embodiments, power module 26 may be coupled to a suitable source of AC or DC power.

Measurement circuitry 28 is coupled to controller 22 and is able to obtain measurements from both metal oxide semiconductor-based hydrogen sulfide gas sensor 30, humidity sensor 32, and temperature sensor 33 and provide digital indications thereof to controller 22. Measurement circuitry 28 may include one or more analog-to-digital converters, suitable multiplexor circuitry, as well as amplification and/or linearization circuitry.

Metal oxide semiconductor-based hydrogen sulfide gas sensor 30 can be any suitable hydrogen sulfide gas sensor that employs metal oxide semiconductor technology. Accordingly, sensor 30 may be a "traditional" metal oxide semiconductor-based hydrogen sulfide gas sensor and NE-MOS based sensor, or any sensor that may be later developed to sense hydrogen sulfide gas using metal oxide semiconductor-based technology.

Humidity sensor 32 is configured to interact with ambient air proximate end 16 and provide an electrical indication of the moisture content in such air. Humidity sensor 32 and temperature sensor 33 are coupled to measurement circuitry 28 such that the electrical indications from sensor 32 and 33 can be measured and provided to controller 22. In this way, controller 22 is able to receive a non-compensated indication of hydrogen sulfide gas concentration from sensor 30, an indication of humidity from humidity sensor 32, temperature indication from temperature sensor 33 and employ a compensation to provide a compensated hydrogen sulfide gas concentration output. As set forth above, in one embodiment, this compensation is performed using a suitable technique and/or calculation(s). However, embodiments of the present invention can be practiced using a lookup table, or other suitable equations. Once controller 22 applies the equation or other suitable compensation to the non-compensated hydrogen sulfide gas sensor reading, a compensated hydrogen sulfide gas concentration is provided via communication circuitry 24. Accordingly, this compensated hydrogen sulfide gas concentration can be provided over a process communication loop or segment to a controller or other suitable device in the process control and monitoring system. Additionally, or alternatively, the compensated hydrogen sulfide gas concentration can be provided as a local output either via a digital indication, and/or an audible or visual alarm.

Figure 3:
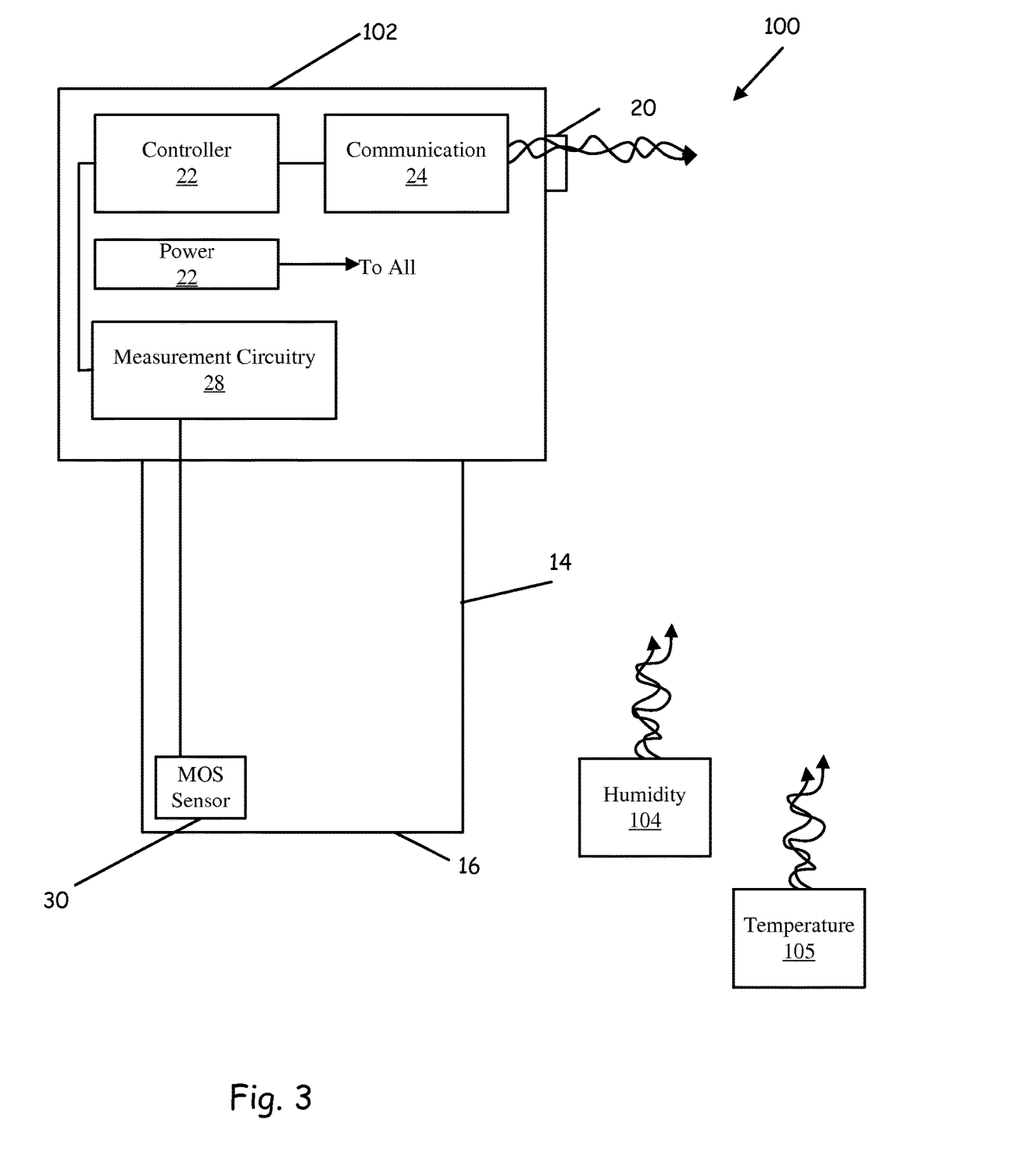
FIG. 3 is a diagrammatic view of a hydrogen sulfide gas detection system in which embodiments of the present invention are particularly useful.

FIG. 3 is a diagrammatic view of a hydrogen sulfide gas detecting system with which embodiments of the present invention are particularly useful. System 100 includes hydrogen sulfide gas detector 102, humidity transmitter 104 and temperature transmitter 105. Detector 102 bares bears many similarities to detector 10 (described with respect to FIG. 2) and like components are numbered similarly. The main distinction between detector 102 and detector 10 is that detector 102 does not include a humidity/temperature sensor. Accordingly, detector 102 may include the hardware of legacy-based hydrogen sulfide gas detectors. However, unlike such legacy detectors, detector 102 includes controller 22 that is able to provide a compensation to the non-compensated metal oxide semiconductor sensor 30 output. In the embodiment shown in FIG. 3, detector 102, humidity transmitter 104, and temperature transmitter 105 are able to provide their respective process variables on a process communication loop or segment. In this way, humidity transmitter 104 and temperature transmitter 105 are entirely separate devices that are able to monitor or otherwise measure the moisture content and temperature, respectively, in ambient air and provide indications of such over a process communication loop or segment. By virtue of communication circuitry 24, device 102 is able to receive the humidity/temperature information and provide such information to controller 22. Controller 22 then applies the received humidity/temperature information to the non-compensated hydrogen sulfide concentration sulfide concentration information received from MOS sensor 30 and provides a humidity/temperature-compensated hydrogen sulfide gas concentration over the process communication loop or segment. Additionally, or alternatively, the compensated hydrogen sulfide gas concentration can be provided at a local operator interlace via a digital indication of concentration, and/or via an audible or visual alarm.

Figure 4:
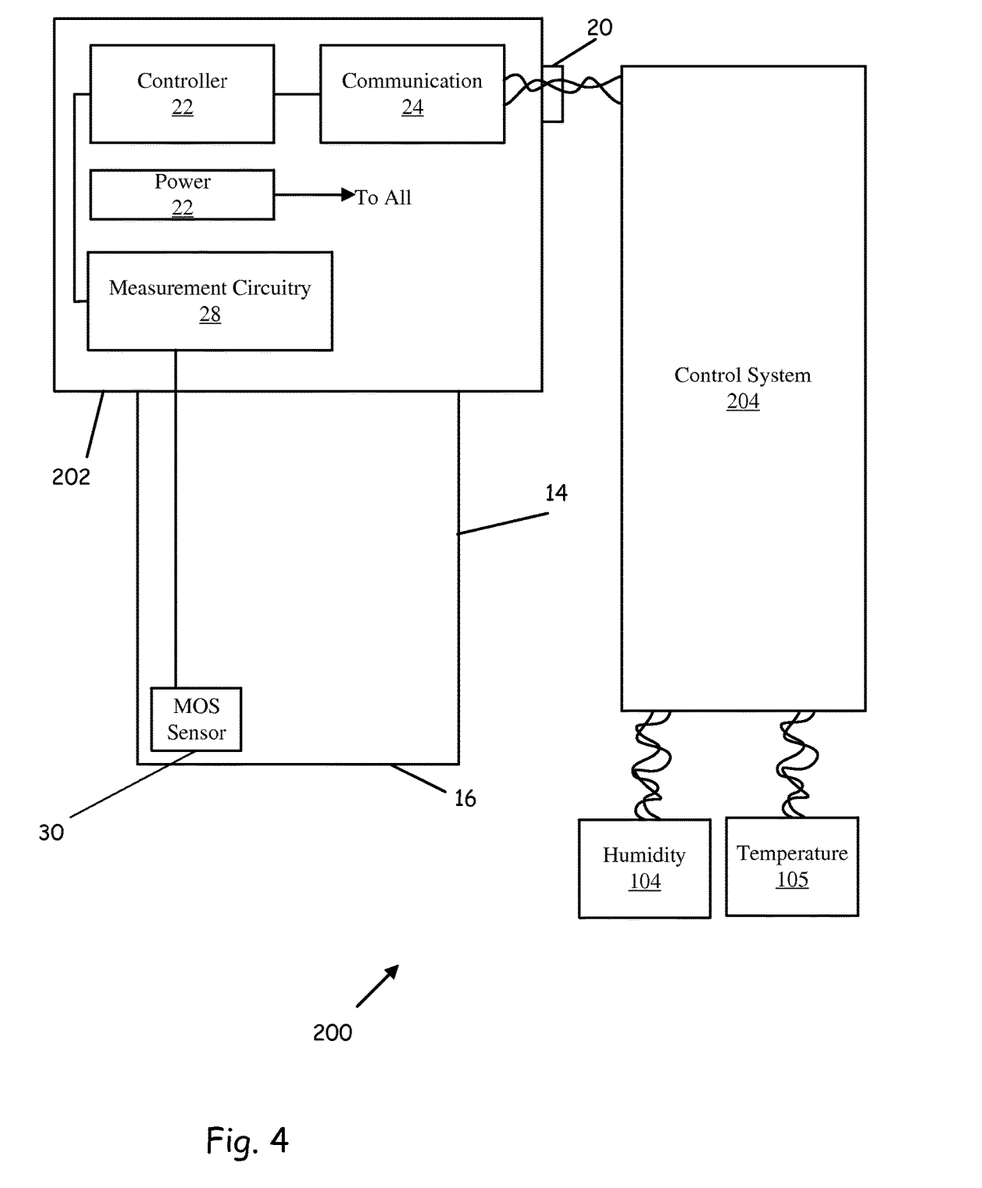
FIG. 4 is a diagrammatic view of a hydrogen sulfide gas detection system in accordance with an embodiment of the present invention.

FIG. 4 is a diagrammatic view of a process control and monitoring system in accordance with an embodiment of the present invention. Process control and monitoring system 200 includes hydrogen sulfide gas detector 202, humidity transmitter 104, and temperature transmitter 105 coupled to control system 204 via one or more process communication loops or segments. In the embodiment illustrated in FIG. 4, each of devices 204, 104, and 105 provides their respective process variables to control system 204 where the non-compensated hydrogen sulfide gas concentration is compensated based on humidity information received from transmitter 104 and temperature information received from temperature transmitter 105. Accordingly, a processor or computer within control system 204 is able to execute the equation set forth above, or other suitable equation or relationship, in order to compensate the hydrogen sulfide gas concentration based on the humidity/temperature information. Additionally, control system 204 may then communicate the compensated hydrogen sulfide gas concentration back to detector 202 such that the compensated concentration can be displayed locally at detector 202.

Figure 5:
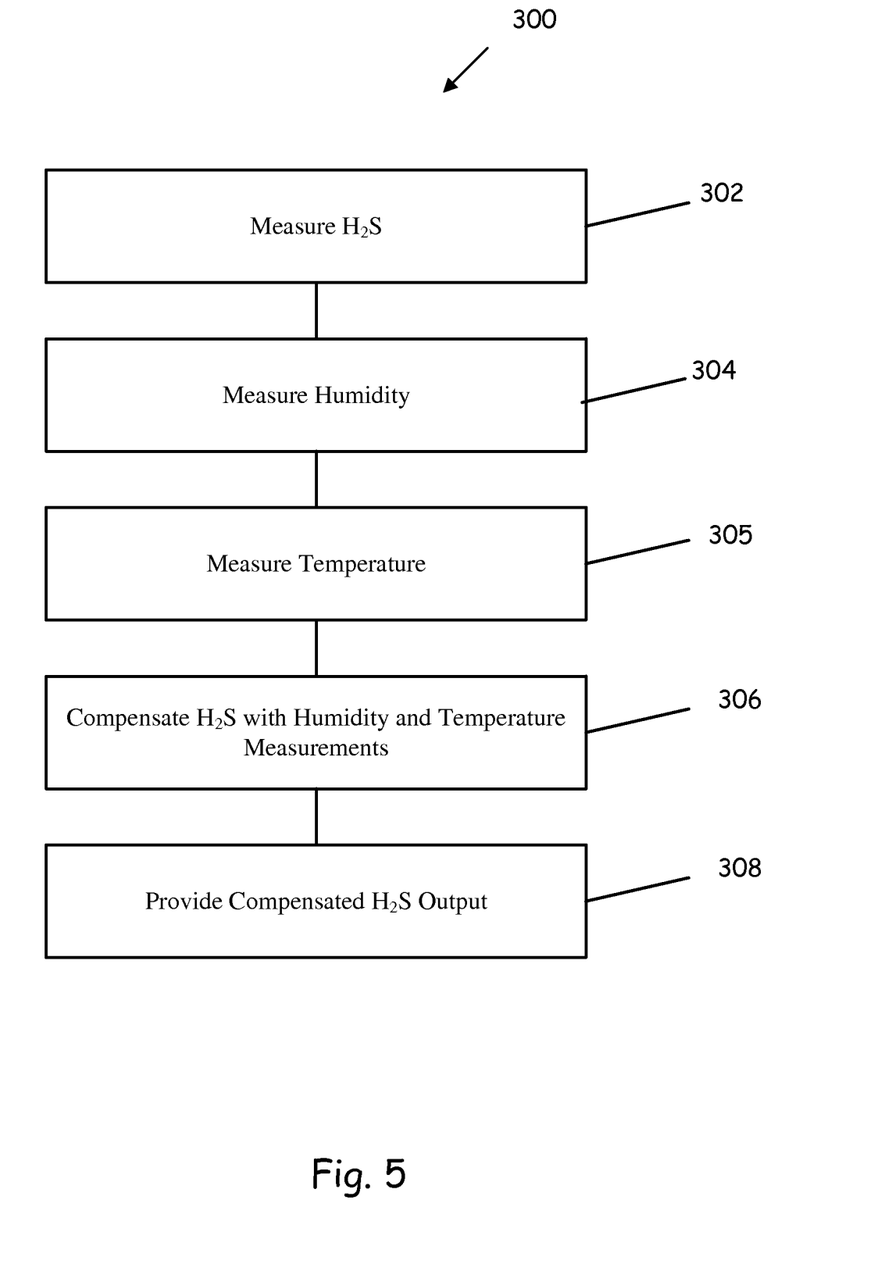
FIG. 5 is a flow diagram of a method of providing a compensated hydrogen sulfide gas measurement in accordance with an embodiment of the present invention.

FIG. 5 is a flow diagram of a method of providing a compensated hydrogen sulfide gas concentration in accordance with an embodiment of the present invention. Method 300 begins at block 302 where a hydrogen sulfide gas concentration is measured using a metal oxide semiconductor-based sensor. Next, at block 304, humidity near the hydrogen sulfide gas sensor is also measured. As set forth above, this humidity measurement may be provided by a humidity sensor disposed within a sensor body of the detector, or it may be provided by an independent humidity measurement system located near the detector. At block 305, the temperature near the hydrogen sulfide gas is measured. As set forth above, this temperature measurement may be provided by a temperature sensor disposed within a sensor body of the detector, or it may be provided by an independent temperature measurement system located near the detector. Next, at block 306, the uncompensated hydrogen sulfide gas concentration is treated with an equation, lookup table, or other suitable relation to compensate for the effects of humidity and temperature in the environment proximate the hydrogen sulfide gas sensor. This compensation can be performed by a controller or other suitable circuitry within a hydrogen sulfide gas detector, or any other suitable device located in or coupled to the process control and monitoring system. Next, at block 308, a compensated hydrogen sulfide gas measurement is provided. This measurement is compensated based on the humidity measurement obtained at block 304 and temperature measurement obtained at block 305. Note, embodiments of the present invention can be practiced where block 304 or block 305 is not executed as frequently as block 302. For example, in environments where the ambient humidity and/or temperature changes much slower than the concentration of hydrogen sulfide gas, block 304 may be executed only periodically, for example, every ten minutes, while block 302 is executed one or more times per second.

Embodiments of the present invention generally permit the empirical, simultaneous measurement of hydrogen sulfide gas concentrations in the presence of humidity in a variety of industrial settings. Moreover, the method and apparatus described herein do not rely on the temperature of the water vapor matching the general ambient environmental conditions. It is believed that embodiments of the present invention may have applicability to technologies that develop refrigerant leak detectors for "green" refrigeration systems based on solid-state sensors. Accordingly, embodiments of the present invention are not limited to the particular gas which is detected, but to the embodiments as set forth in the claims.

Although the present invention has been described with reference to preferred embodiments, workers skilled in the art will recognize that changes may be made in form and detail without departing from the spirit and scope of the invention.

What is claimed is:
1. A hydrogen sulfide gas detector comprising:
a metal oxide semiconductor-based hydrogen sulfide gas sensor having an electrical characteristic that varies with hydrogen sulfide gas concentration;
measurement circuitry, coupled to the metal oxide semiconductor-based hydrogen sulfide gas sensor the measurement circuitry being programmed to measure the electrical characteristic;
communication circuitry programmed to communicate with a process communication loop to receive, through the process communication loop, an ambient tempera- ture from a temperature sensor and an ambient humidity from a remotely located humidity sensor;

a controller, coupled to the measurement circuitry and the communication circuitry, programmed to generate a hydrogen sulfide gas concentration output based on the electrical characteristic, and compensates the hydrogen sulfide gas concentration output by applying a humidity and temperature compensation using a compensation equation that receives the ambient humidity, the ambient temperature, and a solid state sensor resistance as input parameters, and calculates a compensated hydrogen sulfide gas concentration based on input of the input parameters to the compensation equation, generates an output indicative of the compensated hydrogen sulfide gas concentration and provides the output for communication over the process communication loop.

2. A system for monitoring a gas concentration of hydrogen sulfide, the system comprising:

a gas detector further comprising:

a metal oxide semiconductor-based gas sensor having an electrical characteristic that changes based on the is related to the hydrogen sulfide concentration and a temperature, the and a sensitivity to moisture;

measurement circuitry coupled to the metal oxide semiconductor-based gas sensor programmed to measure the electrical characteristic;

a controller, coupled to the measurement circuitry programmed to generate a non-compensated hydrogen sulfide concentration output based on the measured electrical characteristic; and a communication circuitry, coupled to the controller, that communicates on a process communication loop and provides the non-compensated gas concentration output to a process controller;

a humidity measurement system, located remotely from the gas detector, that samples ambient air, obtains the ambient humidity, and communicates the ambient humidity over the process communication loop to the gas detector;

a temperature measurement system, located remotely from the gas detector, that accesses the ambient air, obtains the ambient temperature, and communicates the indication over the process communication loop to the gas detector; and wherein the controller is programmed to calculate a compensated hydrogen sulfide gas concentration, that compensates for effects of ambient humidity and ambient temperature on the non-compensated hydrogen sulfide gas concentration output, by applying the ambient temperature, the ambient humidity, and solid state sensor resistance to a compensation equation, and generates a compensated hydrogen sulfide concentration output that is proportional to the square root of the ambient humidity based on the compensated hydrogen gas concentration.

3. The system of claim 2, wherein the gas detector receives the compensated hydrogen sulfide concentration output via the communication circuitry and provides a local indication of the compensated hydrogen sulfide concentration output.

4. The system of claim 3, wherein the local indication is an alarm.

5. The system of claim 4, wherein the alarm is an audible alarm.

6. The system of claim 4, wherein the alarm is a visual alarm.

7. The system of claim 2, wherein the gas detector is wholly powered by the process communication loop or segment.

* * * * *